(12) United States Patent
Cushman

(10) Patent No.: US 6,256,396 B1
(45) Date of Patent: Jul. 3, 2001

(54) SELF-FITTING HEARING PROTECTION EARPLUG WITH FACILE INSERTION MECHANISM

(76) Inventor: William Bradford Cushman, 1315 Finley Dr., Pensacola, FL (US) 32514

( * ) Notice: Subject to any disclaimer, the term of this patent is extended or adjusted under 35 U.S.C. 154(b) by 0 days.

(21) Appl. No.: 08/451,950

(22) Filed: May 26, 1995

(51) Int. Cl.$^7$ .................................................. H04R 25/00
(52) U.S. Cl. .................... 381/328; 381/322; 381/380; 181/135
(58) Field of Search .................. 381/68, 68.6, 68.3, 381/69, 68.5, 183, 187, 205, 151, 322, 324, 327, 328, 330, 380; 181/129, 130, 135; 128/864, 865

(56) References Cited

U.S. PATENT DOCUMENTS

| | | | |
|---|---|---|---|
| 4,652,702 | * | 3/1987 | Yoshii ................................. 381/151 |
| 5,207,827 | * | 5/1993 | Tokarz ................................. 128/864 |
| 5,333,622 | * | 8/1994 | Casali et al. ......................... 128/864 |
| 5,396,563 | * | 3/1995 | Yoshimi .............................. 381/187 |
| 5,483,027 | * | 1/1996 | Krause ................................ 181/135 |

OTHER PUBLICATIONS

Webster's Third New International Dictionary 1646, 1971.*

* cited by examiner

*Primary Examiner*—Huyen Le

(57) ABSTRACT

A self-fitting hearing protection earplug is disclosed that may be easily inserted or withdrawn from an external auditory meatus by first operating an extension mechanism to reduce the diameter of an expansion bulb of the earplug. Contraction of the expansion bulb of the instant invention allows air to pass by during insertion and removal, thus avoiding the uncomfortable "piston" effect of many current earplug designs. In addition to facile insertion and removal, the earplug of the instant invention may be embedded with fine metallic particles, either alone or according to the teaching of U.S. Pat. No. 5,400,296, to make the earplug easily machine detectable. Furthermore, the earplug of the instant invention may be fitted with a speaker/microphone at the distal end to form the basis of a superior two-way communications system for use in high noise environments.

9 Claims, 2 Drawing Sheets

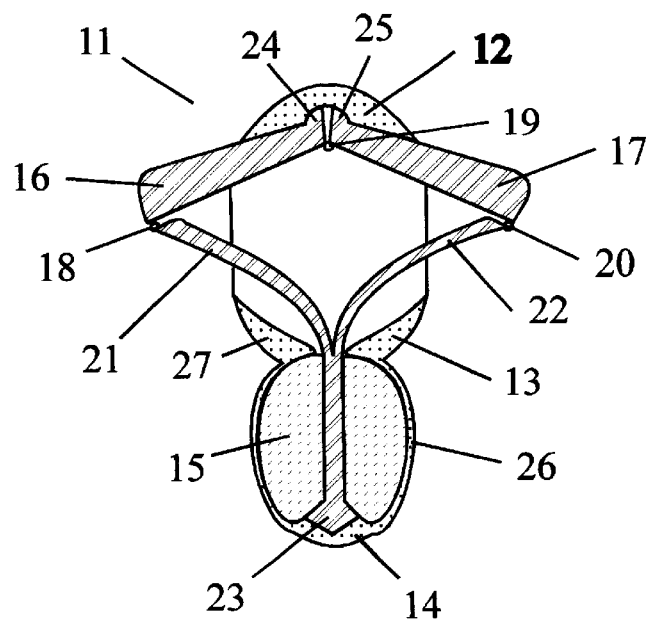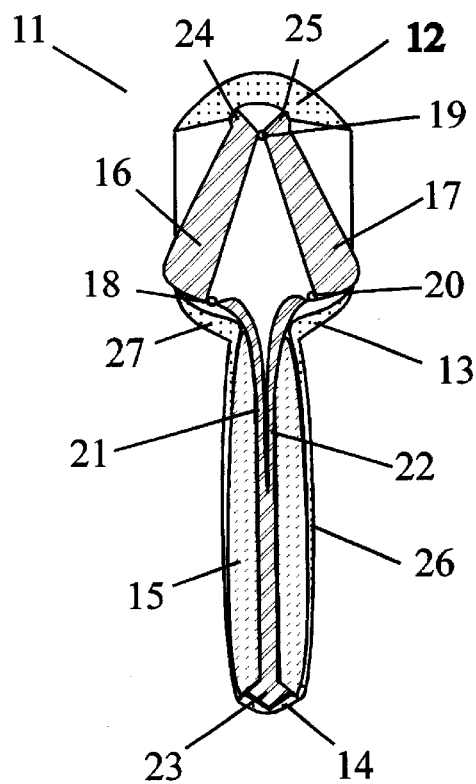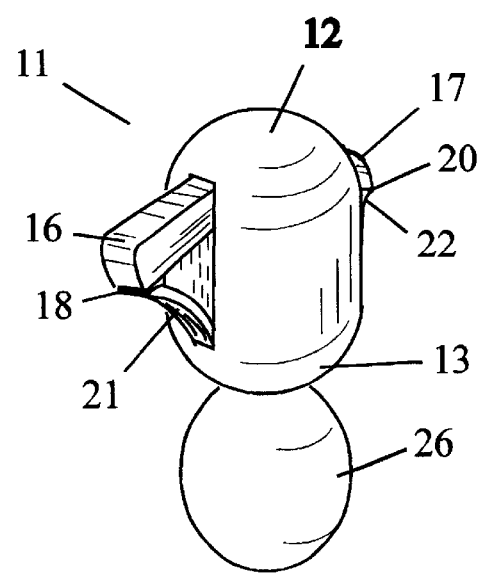

SELF-FITTING HEARING PROTECTION EARPLUG WITH FACILE INSERTION MECHANISM

BACKGROUND OF THE INVENTION

1. Field of the Invention

This invention relates to hearing protection earplugs and more particularly to self-fitting hearing protection earplugs with facile insertion mechanisms which also may possess an integral machine detectability characteristic and also may form the basis for an advanced high-noise environment communications system.

2. Description of Related Art

The need for adequate hearing protection in high noise environments has long been recognized among those concerned with health and safety issues, and much effort has gone into providing such protection. However, most scientists in this field would acknowledge that this effort has not been very successful. Protective devices have proliferated yet remained mediocre in performance. Workers in high noise environments who should use these devices often do not, or use them only under duress from their employers. Individuals that work in high noise environments rarely understand that the effects of high noise exposure are not limited to the moment but are cumulative as well. The lack of worker compliance with safety rules is exacerbated by the fact that currently available hearing protection devices are often uncomfortable, clumsy to use, and perform poorly. It is this second aspect of the problem that can be addressed through technology. Fortunately, as hearing protection devices become more comfortable and perform better, worker compliance with their use should also improve.

Hearing protection devices may be broadly divided into two categories: earcups and earplugs. Earcups are widely used in both industry and in the military. Recently, Poiesis Research, Inc., of Florida, working with the U. S. Navy Aerospace Medical Research Laboratory at Pensacola Fla., demonstrated an advanced earcup design with over 45 dB of attenuation at 100 Hz. This earcup was made possible by advances in materials science described in U.S. Pat. No. 5,400,296, and comes very close to being "perfect" in the sense that it is generally acknowledged that any more than 50 dB of attenuation would be masked by bone conduction and, therefore, superfluous. However, these test results were obtained in a laboratory situation. The earcup was placed against a polished stainless-steel flat-plate coupler that had been lightly coated with vacuum grease to insure a good seal. A real world user will not be likely to apply a coat of grease to insure a seal against his uneven head.

Even a "perfect" earcup will never mate well with the head of the average user, and objectionable noise will simply flank the earcup through leaks at the seal and reduce its effectiveness considerably. Furthermore, earcups of all types always require additional equipment to hold them in place, are heavy, apply pressure to the side of the users head that can cause discomfort, block evaporative cooling over the ears, interfere with other safety devices such as helmets, and may be dangerous in an accident if they are strongly constructed and act like a "cookie cutter."

Ultimately it is always the seal between the hearing protection device and the human using it that limits the overall effectiveness of the hearing protection approach being used. In the case of an earcup, an engineer can do very little about sealing against the user's head. It is the human, not the earcup, that limits this type of hearing protection. Earplugs, however, do not suffer from many of the problems associated with earcups and work within a human/machine interface that is much more amenable to technological improvement. Although the human external auditory meatus is irregular in shape, and contains short fine hairs, it also secretes an excellent sealant, the cerumen or "ear wax." The "ear wax" found on the internal wall of the human external auditory meatus insures that a soft compliant material pressed against it has an excellent chance of forming a very good seal. However, it must be remembered that the distal end of the ear canal contains an exquisitely sensitive pressure transducer that does not tolerate large pressure changes well. Any earplug that seals well may also act as a piston within the external auditory meatus when being inserted or withdrawn and cause discomfort, and sometimes extreme discomfort, as this piston compresses the air or causes a vacuum adjacent to the tympanum. A "perfect" earplug must seal well when in use but not seal or have a pressure release mechanism during insertion or withdrawal.

The "perfect" earplug should also attenuate close to 50 dB over the entire spectrum of audible sound. The materials described in U.S. Pat. No. 5,400,296 suggest that this is a realizable goal, albeit a very difficult one. The "perfect" earplug should be quick and facile to insert and remove. Facile insertion and removal will improve user compliance with hearing protection requirements in high noise environments. Three other aspects of the "perfect" earplug can be posed as design targets: a) The "perfect" earplug should be machine detectable so that if it should, for example, fall into a batch of cereal at a processing plant it can be easily retrieved. b) The design of the "perfect" earplug should be amenable to use as part of a two way communications device for high noise environments. And, c) The "perfect" earplug must be manufacturable. Experiments at Poiesis Research, Inc. have shown that when a microphone is placed in the external auditory meatus and shielded from external noise the same mechanisms that provide 50 dB of auditory shielding for the tympanum work for the microphone as well. The subject's vocal cords are acoustically coupled to the external auditory meatus and his voice is available for pickup by the microphone within this canal. Conversely, many microphone designs will also work as speakers, thus providing the basis for an excellent two-way communications system sealed into the external auditory meatus.

Prior art earplugs all fall short of the ideal posed above. For example, U.S. Pat. No. 2,246,737 shows an earplug made of resilient material with projecting annular fins which deform and engage the internal surfaces of the external auditory meatus. This earplug and its many related "annular fin" designs act as a piston within the external auditory meatus when being inserted and withdrawn, thus causing sometimes painful pressure differentials across the tympanum. U.S. Pat. No. 3,881,570 shows a self-fitting earplug that must be manually elongated by rolling between the fingers and stretching before insertion in the external auditory meatus where it will slowly contract lengthwise and expand radially to fill and seal the canal. The putty-like material within this earplug must be stiff and have a very slow recovery time to allow sufficient time for insertion after it has been elongated, thus making it difficult to elongate in the first place and making the time lag between insertion and sealing quite long and incomplete. Furthermore, this design also acts as a piston when being withdrawn. U.S. Pat. No. 4,089,332 shows a pneumatic shaping earplug with some promise, but this design is limited in the ratio of contracted to expanded states by the mechanism involved to a rather small difference. This design will also act as a piston when withdrawn, and possibly when inserted. U.S. Pat. No. 4,060, 080 shows an earplug design that is much closer to the ideal proposed above except that it is necessarily liquid-filled and liquids are very poor attenuators. Furthermore, the design shown in U.S. Pat. No. 4,060,080 would be difficult to manufacture.

SUMMARY OF THE INVENTION

Accordingly, an object of the instant invention is to provide an improved earplug that is amenable to the use of bulk acoustic attenuation and vibration damping of materials as described in U.S. Pat. No. 5,400,296.

Another object of the instant invention is to provide an improved earplug that is facile to both insert and withdraw without acting as a piston within the external auditory meatus and causing pressure differentials at the tympanum.

Another object of the instant invention is to provide an improved earplug that quickly self-fits within the external auditory meatus without undue discomfort for the user.

Another object of the instant invention is to provide an improved earplug that is readily detectable and retrievable by machines.

Another object of the instant invention is to provide an improved earplug that can act as the basis of an improved two-way communications system for use in high-noise environments.

A further object of the instant invention is to provide an improved earplug that is readily manufacturable.

These and additional objects of the invention are accomplished by an earplug made from materials as described in U.S. Pat. No. 5,400,296 where at least one of the species of particles used within the material is a machine detectable particle such as iron, where the earplug is caused to extend lengthwise and contract radically for insertion or removal from the external auditory meatus by an extension device, where the inherent lengthwise contraction of the elongated earplug when the extension device is released causes the earplug to expand radially and self-fit within the external auditory meatus of the user, and where the distal end of the extension device may be comprised of a microphone/speaker as part of a two-way communications system.

BRIEF DESCRIPTION OF THE DRAWINGS

In the following Description of the Preferred Embodiments and the accompanying drawings, like numerals in different figures represent the same structures or elements. The representation in each of the figures is diagrammatic and no attempt is made to indicate actual scales or precise ratios. Proportional relationships are shown as approximations.

FIG. 1 shows a cross-sectional view of a preferred embodiment of the instant invention with expansion bulb expanded.

FIG. 2 shows a cross-sectional view of a preferred embodiment of the instant invention with expansion bulb extended lengthwise and radially contracted.

FIG. 3 shows a perspective view of a preferred embodiment of the instant invention with expansion bulb expanded.

DESCRIPTION OF THE PREFERRED EMBODIMENTS

Figure 4:
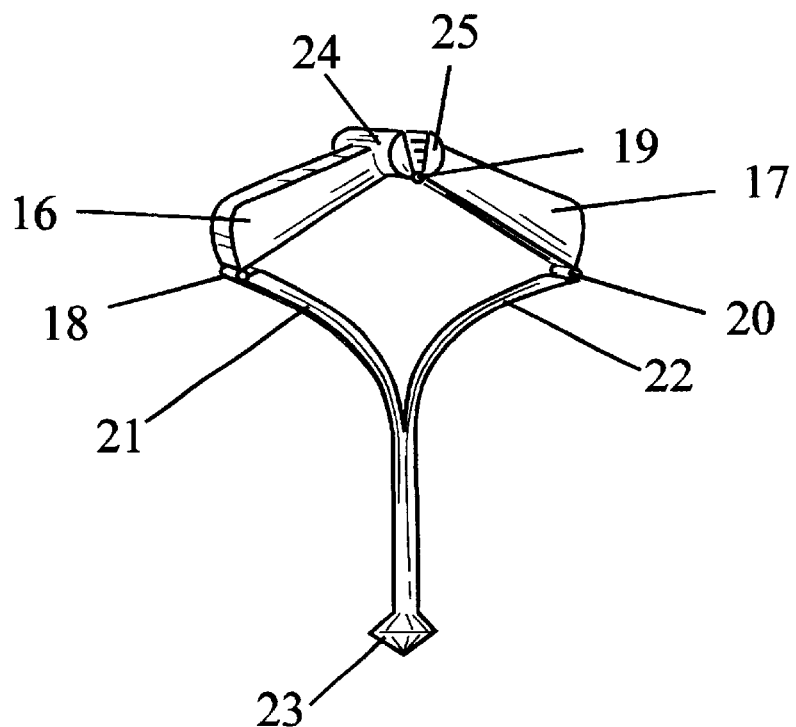
FIG. 4 shows a perspective view of the extensor mechanism of a preferred embodiment of the instant invention.

The parts indicated on the drawings by numerals are identified below to aid in the reader's understanding of the present invention.

11. Earplug.
12. Upper body.
13. Neck region.
14. Distal end.
15. Gel.
16. Extensor wing.
17. Extensor wing.
18. Hinge.
19. Hinge.
20. Hinge.
21. Leg of bifurcated shaft.
22. Leg of bifurcated shaft.
23. Bifurcated shaft tip.
24. Catch.
25. Catch.
26. Expansion bulb.
27. Machine detectable particles.
28. Microphone/speaker lead.
29. Microphone/speaker.
30. Diaphragm.

A preferred embodiment of the instant invention is shown in cross-sectional view in FIG. 1 with expansion bulb expanded. In FIG. 1, 11 is the earplug, 12 is an upper body, 13 is a neck region, 26 is an expansion bulb which is insertable within the external auditory meatus of a person using the instant invention, and 14 shows a distal end of an earplug body that could be molded as a single molding from a suitable elastomeric material such as silicone rubber. Within the expansion bulb, 26, is a low-durometer gel, 15, which may contain machine detectable particles such as iron, alone or according to the teaching of U.S. Pat. No. 5,400,296 to form a bulk acoustic attenuator from the elastomeric material used. The elastomeric material used for the earplug body may also contain machine detectable particles, 27, such as iron, alone or according to the teaching of U.S. Pat. No. 5,400,296 to form a bulk acoustic attenuator from the material used.

Within the earplug, 11, of FIG. 1 an extension mechanism is shown that may be molded as a single molding and may also benefit from the technology taught in U.S. Pat. No. 5,400,296; comprised of an extensor wing, 16, connected through a hinge, 19, to a second extensor wing, 17, and connected to two legs of a bifurcated shaft, 21 and 22, through hinges 18 and 20 respectively. The bifurcated shaft terminates at a expanded bifurcated shaft tip, 23. The extensor wings, 16 and 17, have catches, 24 and 25, molded to the ends hinged at 19 to catch the elastomeric material of the earplug body near 12 so that the elastic properties of the upper earplug body will act as a return spring for the extensor wings, 16 and 17, when they are caused to pivot upon hinge, 19. Hinge, 19, is offset toward the distal end, 14, of earplug, 11, to improve the return spring action of catches 24 and 25. Hinges, 18, 19, and 20 are formed from thin portions of the extension mechanism, which is made from a semi-flexible material such as Nylon.

FIG. 2 shows the preferred embodiment of the instant invention shown in cross-sectional view in FIG. 1 with expansion bulb extended. In FIG. 2, 11 is the earplug, 12 is an upper body, 13 is a neck region, 26 is an expansion bulb which is insertable within the external auditory meatus of a person using the instant invention, and 14 shows a distal end of an earplug body that could be molded as a single molding from a suitable elastomeric material such as silicone rubber.

Within the expansion bulb, 26, is a low-durometer gel, 15, which may contain machine detectable particles such as iron, alone or according to the teaching of U.S. Pat. No. 5,400,296 to form a bulk acoustic attenuator from the elastomeric material used. The elastomeric material used for the body of earplug, 11, may also contain machine detectable particles, 27, such as iron, alone or according to the teaching of U.S. Pat. No. 5,400,296 to form a bulk acoustic attenuator from the material used.

Within the earplug, 11, of FIG. 2 an extension mechanism is shown that may be molded as a single molding and may also benefit from the technology taught in U.S. Pat. No. 5,400,296; comprised of an extensor wing, 16, connected through a hinge, 19, to a second extensor wing, 17, and connected to two legs of a bifurcated shaft, 21 and 22, through hinges 18 and 20 respectively. The bifurcated shaft terminates at a expanded bifurcated shaft tip, 23. The extensor wings, 16 and 17, have catches, 24 and 25, molded to the ends hinged at 19 to catch the elastomeric material of the earplug body near 12 so that the elastic properties of the upper earplug body will act as a return spring for the extensor wings, 16 and 17, when they are caused to pivot upon hinge, 19. Hinge, 19, is offset toward the distal end, 14, of earplug, 11, to improve the return spring action of catches 24 and 25.

The extension of the expansion bulb, 26, shown in FIG. 2 is an extension ratio of slightly over two to one. If the diameter of the bifurcated shaft shown in FIG. 2 is two millimeters and the original diameter of the expansion bulb, 26, before extension was ten centimeters, then the resulting reduction in radial cross-sectional area will exceed 50%. An expansion/contraction ratio of over 50% gives a very comfortable design margin so that an earplug can be sized to a large number of individuals.

FIG. 3 shows a perspective view of a preferred embodiment of the instant invention with expansion bulb expanded. In FIG. 3 11 is the earplug, 12 is an upper body, 13 is a neck region, and 26 is an expansion bulb which is insertable within the external auditory meatus of a person using the instant invention. Within the earplug, 11, of FIG. 3 an extension mechanism is partially shown; comprised of an extensor wing, 16, connected through a hinge to a second extensor wing, 17, and to two legs of a bifurcated shaft, 21 and 22, through hinges 18 and 20 respectively.

FIG. 4 shows a perspective view of the extension mechanism of a preferred embodiment of the instant invention. The extension mechanism may be made from a semi-flexible polymer such as Nylon as a single molding, and treated according to the teachings of U.S. Pat. No. 5,400,296 to become a bulk acoustic energy absorber. For safety reasons, the extension mechanism of the preferred embodiment of the instant invention is flexible and designed so that a blow to the side of a user's head would cause the extension mechanism to flatten and shorten the bifurcated shaft rather than extend it into the external auditory meatus. In FIG. 4 an extension mechanism is shown that is comprised of an extensor wing, 16, connected through a hinge, 19, to a second extensor wing, 17, and connected to two legs of a bifurcated shaft, 21 and 22, through hinges 18 and 20 respectively. The bifurcated shaft terminates at a expanded bifurcated shaft tip, 23. The extensor wings, 16 and 17, have catches, 24 and 25, molded to the ends hinged at 19 to catch the elastomeric material of the earplug body so that the elastic properties of the upper earplug body will act as a return spring for the extensor wings, 16 and 17, when they are caused to pivot upon hinge, 19. Hinge, 19, is offset toward the bifurcated shaft tip, 23, to improve the return spring action of catches 24 and 25. Hinges, 18, 19, and 20 are formed from thin portions of the extension mechanism.

Figure 5:
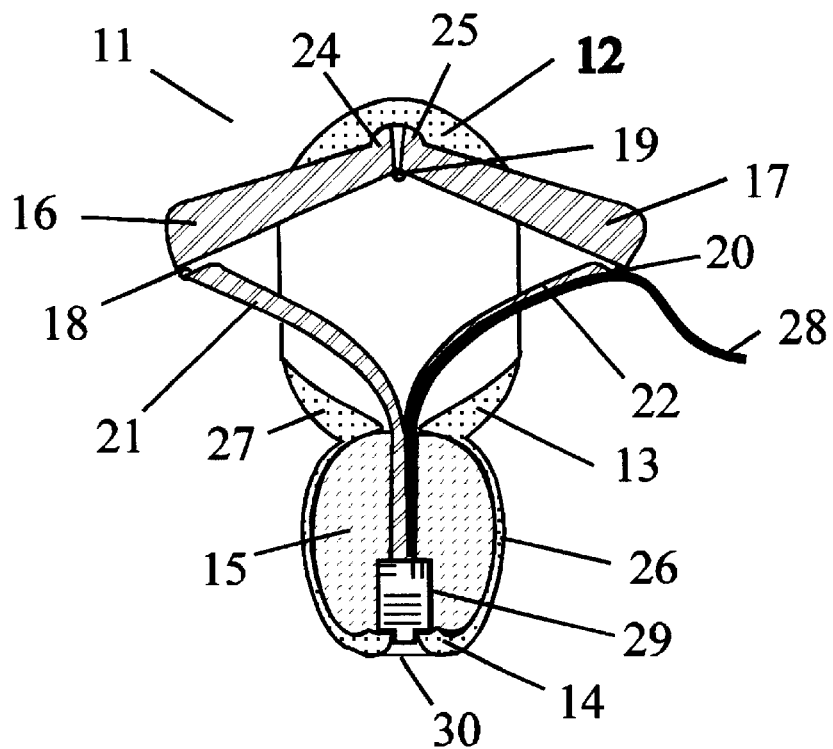
FIG. 5 shows a cross-sectional view of a preferred embodiment of the instant invention as it may be modified to become part of a two-way communications system.

FIG. 5 shows a cross-sectional view of a preferred embodiment of the instant invention as it may be modified to become part of a two-way communications system. FIG. 5 is identical to FIG. 1 except that bifurcated shaft tip, 23, has been replaced with microphone/speaker, 29; the distal end of earplug, 11, at 14, has been opened up to allow acoustic pressure to pass to and from microphone/speaker, 29; diaphragm, 30, has been added to aid in preventing contamination of microphone/speaker, 29, by foreign materials; and speaker/microphone lead, 28, has been molded into bifurcated shaft leg, 22. Drivers and electronics for microphone/speaker, 29, are beyond the scope of this application but are well within the skills of professionals within this art. A suitable microphone/speaker for this application could be the EH 12C model 3060 balanced armature type manufactured by Knowles Electronics, Inc. of Itasca, Ill. This microphone/speaker was designed for in-the-ear applications and measures only 3.58 by 3.02 millimeters by 5.21 millimeters long. Placement of a microphone/speaker at the location shown in the preferred embodiment of FIG. 5 allows the microphone/speaker to benefit form the acoustic shielding of the earplug as well as the acoustic shielding of the human using it. The human's acoustic shielding amounts to some 50 dB. However, the human voice is well coupled acoustically to the tympanum, making a two-way communications system suitable for high noise environments using a shielded in-the-ear canal microphone and speaker much superior to approaches that attempt to pick up voice at the mouth or throat.

Many modifications and variations of the present invention are possible in light of the above teachings. For example, the extension mechanism of the preferred embodiment of the instant invention could be as simple as a shaft protruding form the proximal end of the earplug which the user inserts with a finger, and the expansion bulb of the instant invention could be made entirely made of a low durometer elastomer with no separate gel. It is therefore to be understood that, within the scope of the appended claims, the instant invention may be practiced otherwise than as specifically described.

I claim:

1. A self-fitting hearing protection earplug comprised of:
   a) an earplug body with an attached expansion bulb; and,
   b) an expansion bulb extension mechanism comprised of a bifurcated shaft pivotably attached at the ends of each leg of said bifurcated shaft to the ends of extensor wings, said extensor wings being centrally pivotably attached, with the distal end of said bifurcated shaft disposed at or near the internal surface of said earplug expansion bulb and the proximal end of said extensor wing central pivotable attachment disposed at or near the internal surface of the proximal end of said earplug body;

whereby rotating said extensor wing mechanisms about said central pivotable attachment causes the ends of each leg of said bifurcated shaft to close together and extend the distal end of said bifurcated shaft against the internal surface of said earplug expansion bulb, and to press against the internal surface of the earplug body at the proximal end of said central pivotable attachment, and lengthwise extension of said expansion bulb by the operation of said extension mechanism causes radial contraction of said expansion bulb, thereby allowing said expansion bulb of said self-fitting hearing protection earplug to be easily inserted or removed within an external auditory meatus, and return of said extension mechanism to a non-extended position allows said expansion bulb to expand and self-fit within an external auditory meatus when said expansion bulb of said self-fitting hearing protection earplug is disposed therein.

2. The self-fitting hearing protection earplug of claim 1 where said expansion bulb is comprised of an elastomeric envelope.

3. The self-fitting hearing protection earplug of claim 2 where said elastomeric envelope contains an elastomeric material.

4. The self-fitting hearing protection earplug of claim 2 where said elastomeric envelope contains a gel.

5. The self-fitting hearing protection earplug of claim 1 with a speaker/microphone at the distal end whereby said hearing protection earplug provides acoustic shielding for said speaker/microphone when said hearing protection earplug is disposed within an external auditory meatus.

6. The hearing protection earplug with a speaker/microphone of claim 5 where said speaker/microphone is a speaker only.

7. The hearing protection earplug with a speaker/microphone of claim 5 where said speaker/microphone is a microphone only.

8. A hearing protection earplug comprised of materials with embedded metallic particles whereby said hearing protection earplug may be easily machine detectable.

9. The hearing protection earplug of claim 8 where said embedded metallic particles are iron.

* * * * *